US00PP37345P3

(12) United States Plant Patent
Schoone

(10) Patent No.: US PP37,345 P3
(45) Date of Patent: Mar. 24, 2026

(54) ***PHALAENOPSIS* PLANT NAMED 'Talk Show'**

(50) Latin Name: *Phalaenopsis hybrida*
Varietal Denomination: Talk Show

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/243,682

(22) Filed: Jun. 19, 2025

(65) Prior Publication Data

US 2025/0393488 P1 Dec. 25, 2025

Related U.S. Application Data

(60) Provisional application No. 63/662,415, filed on Jun. 20, 2024.

(51) Int. Cl.
*A01H 6/62* (2018.01)
*A01H 5/02* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Talk Show', characterized by its upright plant habit; relatively strong flowering stems; healthy and sturdy leaves; freely flowering habit with typically two inflorescences developing per plant, each inflorescence with numerous flowers; 'big lip" type flowers with pale purple-colored flower petals and sepals that are heavily overlain with reddish purple-colored stripes and netting; and good post-production longevity.

2 Drawing Sheets

Botanical designation: *Phalaenopsis hybrida.*

Figure 1:
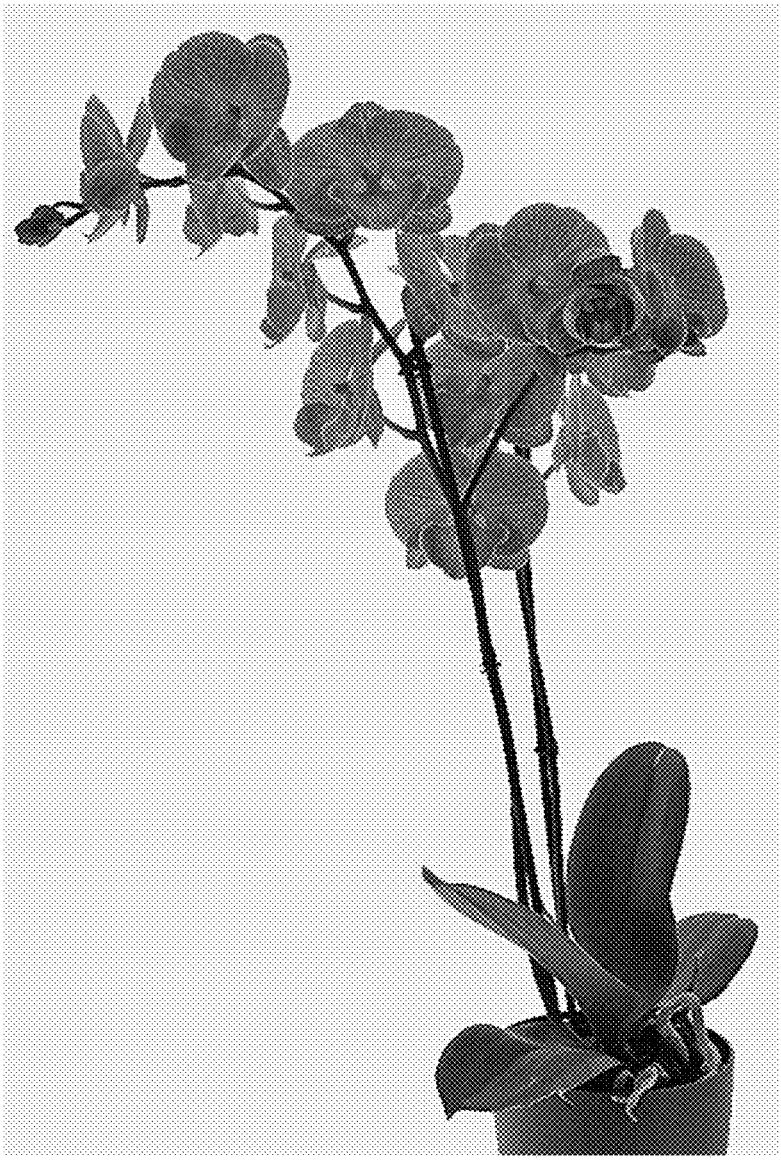

Cultivar denomination: 'TALK SHOW'. CROSS-REFERENCED TO CLOSELY-RELATED APPLICATIONS:

A European Community Plant Breeder's Rights application for the instant plant was filed by the Applicant/Assignee, Floricultura B.V. of Heemskerk, The Netherlands on Jun. 7, 2024, application number 2024/1307. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Talk Show'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in January, 2014 in Assendelft, The Netherlands of *Phalaenopsis hybrida* 'Big Class', not patented, as the female, or seed, parent with a proprietary selection of *Phalaenopsis hybrida* identified as a crossing between 'Maki Watanabe' x 'Hilo Lip', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in July, 2020.

Asexual reproduction of the new *Phalaenopsis* plant by in vitro meristem propagation in a controlled environment in Assendelft, The Netherlands since June, 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Talk Show'. These characteristics in combination distinguish 'Talk Show' as a new and distinct *Phalaenopsis* plant:

1. Upright plant habit.
2. Relatively strong flowering stems.
3. Healthy and sturdy leaves.
4. Freely flowering habit with typically two inflorescences developing per plant, each inflorescence with numerous flowers.
5. 'Big lip" type flowers with pale purple-colored flower petals and sepals that are heavily overlain with reddish purple- colored stripes and netting.
6. Good postproduction longevity.

Plants of the new *Phalaenopsis* can be compared to plants of the female parent, 'Big Class'. Plants of the new *Phalaenopsis* differ primarily from plants of 'Big Class' in petal arrangement as flower petals of plants of the new *Phalae-*

*nopsis* are imbricate whereas the flower petals of plants of 'Big Class' are not imbricate. In addition, flowers of plants of the new *Phalaenopsis* are more densely covered in stripes and netting than flowers of plants of 'Big Class'.

Plants of the new *Phalaenopsis* can be compared to plants of the male parent selection. Plants of the new *Phalaenopsis* differ primarily from plants of the male parent selection in labella form as flowers of plants of the new *Phalaenopsis* are "big lip" types whereas flowers of plants of the male parent selection are not "big lip" types. In addition, flowers of plants of the new *Phalaenopsis* are more densely covered in stripes and netting than flowers of plants of the male parent selection.

Plants of the new *Phalaenopsis* can be compared to plants of *Phalaenopsis hybrida* 'Sweet Talk', not patented. In side-by-side comparisons, plants of the new *Phalaenopsis* differ primarily from plants of 'Sweet Talk' in the following characteristics:

1. Leaves of plants of the new *Phalaenopsis* are darker green in color than leaves of plants of 'Sweet Talk'.
2. Leaves of plants of the new *Phalaenopsis* do not have any apparent anthocyanin whereas leaves of plants of 'Sweet Talk' have apparent anthocyanin.
3. The column color of flowers of plants of the new *Phalaenopsis* is mostly violet whereas the column color of flowers of plants of 'Sweet Talk' is white.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Talk Show' grown in a container.

Figure 2:
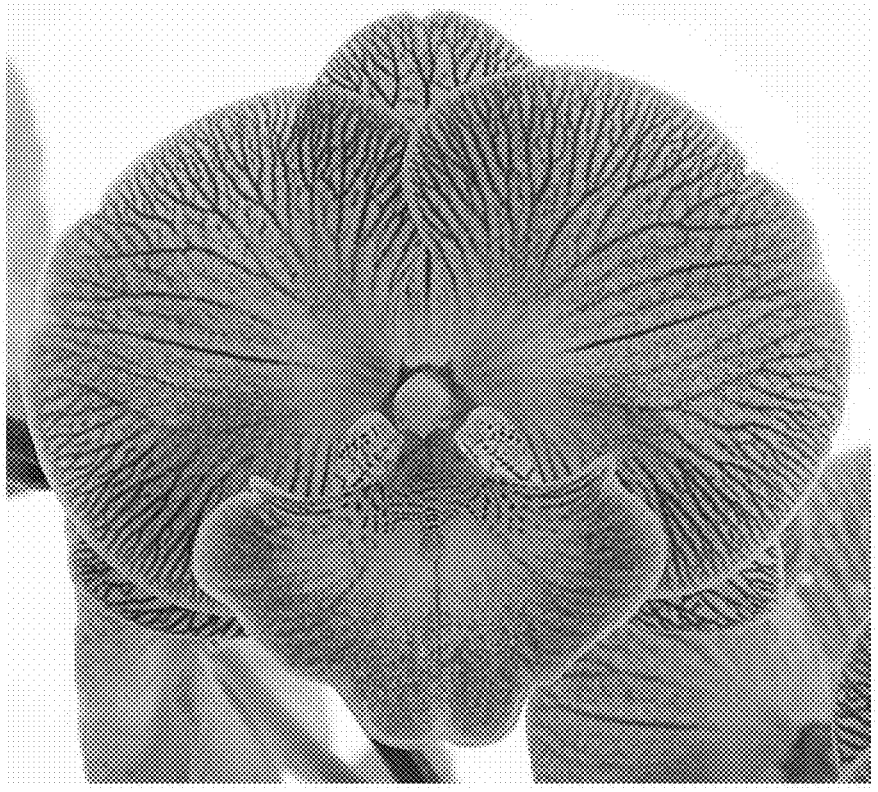

The photograph on the second sheet (FIG. 2) is a close-up view of a typical flower of 'Talk Show'.

DETAILED BOTANICAL DESCRIPTION

The aforementioned photographs and following observations and measurements describe plants grown during the summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Talk Show'.

Parentage:

*Female, or seed, parent.*—*Phalaenopsis hybrida* 'Big Class', not patented.

*Male, or pollen, parent*.—Proprietary selection of *Phalaenopsis hybrida* identified as a crossing between 'Maki Watanabe' x 'Hilo Lip', not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; relatively moderately vigorous to vigorous growth habit and moderate growth rate.

*Plant height, substrate level to top of foliar plane*.—About 16.5 cm.

*Plant height, substrate level to top of floral plane*.—About 50.8 cm.

*Plant diameter or spread*.—About 29.6 cm.

Leaf description:

*Arrangement and quantity*.—Distichous, simple; sessile; about five to six fully-developed leaves per plant.

*Length*.—About 17.4 cm.

*Width*.—About 6.7 cm.

*Aspect*.—Semi-erect to horizontal and outwardly arching.

*Shape*.—Narrowly obovate; slightly carinate.

*Apex*.—Unequal acute.

*Base*.—Sheathing. Sheath length: About 1.2 cm. Sheath width: About 1 cm. Sheath color, upper and lower surfaces: Close to 143B to 143C.

*Margin*.—Entire.

*Texture and luster, upper surface*.—Smooth, glabrous; slightly glossy.

*Texture and luster, lower surface*.—Smooth, glabrous; slightly glossy to matte.

*Venation pattern*.—Camptodromous.

*Color*.—Developing leaves, upper surface: Close to between NN137A and 147A. Developing leaves, lower surface: Close to 146B; towards the margins, close to 147D. Fully expanded leaves, upper surface: Close to NN137A; venation, close to 146A. Fully expanded leaves, lower surface: Close to 146A; towards the margins, close to NN137A; venation, close to 143B.

Inflorescence description:

*Appearance and flowering habit*.—Showy zygomorphic flowers arranged on axillary simple or branched racemes; typically two inflorescences develop per plant; each inflorescence with about ten flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about seven weeks on the plant; flowers not persistent.

*Inflorescence length* (*lowermost flower to inflorescence apex*).—About 24.4 cm.

*Inflorescence width*.—About 26.7 cm.

*Flower buds*.—Height: About 1.8 cm. Diameter: About 1.4 cm by 1.5 cm. Shape: Broadly ovate. Color: Close to 152D, moderately to strongly tinged with close to 182C.

*Flower size*.—About 8.3 cm (vertical) by 8.6 cm (horizontal).

*Flower depth*.—About 3 cm.

*Petals, quantity and arrangement*.—Three, two lateral petals and one center petal transformed into a labellum.

*Lateral petals*.—Length: About 4.1 cm. Width: About 6.2 cm. Shape: Lunate to reniform; not fused; imbricate. Apex: Broadly and shallowly retuse. Margin: Entire. Texture and luster, upper surface: Smooth, glabrous; velvety; matte. Texture and luster, lower surface: Smooth, glabrous; velvety; slightly glossy. Color: When opening, upper surface: Ground color, close to NN155D with fine mottling, close to N78B; at the base, close to NN74B; venation, N78A. When opening, lower surface: Ground color, close to N155B; towards the apex and margins, tinged with close to N75A and N75B; at the base, close to NN74B; venation, close to N78A. Fully opened, upper surface: Ground color, close to 84D with fine mottling, close to N78C and NN78D; narrow marginal edges, close to NN155D; at the base, close to NN74B; venation, close to between N78A and NN78A. Fully opened, lower surface: Ground color, close to between 76D and N155A; towards the apex and margins, tinged with close to N75D; narrow marginal edges, close to NN155D; at the base, close to NN74B; venation, close to N78A.

*Labella*.—Appearance: Lateral and central lobes fused forming a "big lip" type labella. Length: About 3.7 cm. Width: About 4.8 cm. Shape: Broadly rhomboid to reniform in overall outline; moderately concave. Apex: Broadly retuse with two short cirrhose apices. Margins: Entire. Texture and luster, upper and lower surfaces: Smooth, glabrous, moderately velvety; matte. Callosities: Located at the base of the labellum and attachment point of the lateral petals; about 1 cm in length, about 6 mm in width and about 8 mm in height. Color: When opening, upper surface: Close to N78A to N78B; towards the margins and base, close to between N155A to NN155D; narrow marginal edges, close to NN155D; at the base, dots and stripes, close to N78A to N78B; venation, close to NN78A. When opening, lower surface: Close to NN155D; towards the margins, close to N78B to N78C; venation, close to N78B. Fully opened, upper surface: Close to between N78C and NN78C; towards the margins and base, close to between N155A to NN155D; narrow marginal edges, close to NN155D; at the base, dots and stripes, close to N78A to N78B; venation, close to NN78A. Fully opened, lower surface: Close to NN155D; towards the margins, close to N78D; venation, close to N78B to N78C. Color, callosities: When developing and fully developed: Close to N155A with fine dots, close to N78A to N78B.

*Sepals*.—Quantity and arrangement: Three, one upper dorsal sepal and two lower lateral sepals. Length, dorsal sepal: About 4.4 cm. Width, dorsal sepal: About 3.6 cm. Length, lateral sepals: About 4.6 cm. Width, lateral sepals: About 3 cm. Shape, dorsal sepal: Obovate to elliptic. Shape, lateral sepals: Ovate. Apex, dorsal sepal: Obtuse. Apex, lateral sepals: Broadly and bluntly acute. Base, dorsal and lateral sepals: Truncate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to NN155D with fine mottling, close to N78B and N78C; at the base, close to NN74B; venation, close to between N78A and NN78A. When opening, lower surface: Close to between 75D and 156D; towards the apex and margins, close to 76B; venation, close to N78A to N78B. Fully opened, upper surface: Close to NN155D with fine mottling, close to N78B; at the base, close to NN74B; venation, close to between N78A and NN78A. Fully opened, lower surface: Close to between 75D and 156D; towards the apex and margins, close to 76B; venation, close to N78A to N78B. Color, lateral sepals: When opening, upper surface: Close to NN155D with fine mottling, close to NN78B and NN78C; at the base, close to 150D; venation, close to between N78A and NN78A. When opening, lower surface: Close to 195D; marginal venation, close to N77B. Fully opened, upper surface: Close to NN155D with fine mottling, close to N78B; venation, close to between N78A and NN78A; colors do not change with subsequent development. Fully opened, lower surface: Close to between 150D and 195D; marginal venation, close to 75A.

*Peduncles*.—Length: About 55.3 cm. Diameter: About 6 mm. Strength: Strong. Aspect: Upright to outwardly arching. Texture and luster: Smooth, glabrous; matte. Color: Close to 147A with fine dots, close to 143B.

*Pedicels*.—Length: About 3.7 cm. Diameter: About 3 mm. Strength: Moderately strong. Aspect: About 65° from peduncle axis. Texture and luster: Smooth, glabrous; matte. Color: Close to 196A to 196C; distal end, close to 76D; proximal end, close to 148A.

*Reproductive organs*.—Androecium: Column length: About 9 mm. Column width: About 6 mm. Column color: Close to between N78B and NN78C; at the apex, close to NN155B. Pollinia quantity: Two. Pollinia diameter (per two pollinia): About 2 mm. Pollinia color: Close to 24A. Gynoecium: Stigma length: About 2.5 mm. Stigma width: About 4 mm. Stigma shape: Reniform. Stigma color: Close to N155A. Ovary length: About 7 mm. Ovary diameter: About 1 mm. Ovary color: Close to 155A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Talk Show' as herein illustrated and described.

* * * * *